United States Patent
Kort et al.

(10) Patent No.: US 12,214,005 B2
(45) Date of Patent: *Feb. 4, 2025

(54) PROBIOTIC COMPOSITION FOR PREVENTION OF BACTERIAL VAGINOSIS

(71) Applicant: NEDERLANDSE ORGANISATIE VOOR TOEGEPAST-NATUURWETENSCHAPPELIJK ONDERZOEK TNO, DA's-Gravenhage (NL)

(72) Inventors: Remco Kort, Amsterdam (NL); Charlotte Van Der Veer, Blantyre (MW)

(73) Assignee: NEDERLANDSE ORGANISATIE VOOR TOEGEPAST-NATUURWETENSCHAPPELIJK ONDERZOEK TNO, DA's-Gravenhage (NL)

(*) Notice: Subject to any disclaimer, the term of this patent is extended or adjusted under 35 U.S.C. 154(b) by 68 days.

This patent is subject to a terminal disclaimer.

(21) Appl. No.: 17/819,476

(22) Filed: Aug. 12, 2022

(65) Prior Publication Data

US 2022/0378856 A1 Dec. 1, 2022

Related U.S. Application Data

(63) Continuation of application No. 16/628,762, filed as application No. PCT/NL2018/050479 on Jul. 12, 2018, now Pat. No. 11,446,343.

(30) Foreign Application Priority Data

Jul. 12, 2017 (EP) .................................... 17181005

(51) Int. Cl.
| | | |
|---|---|---|
| *A61K 35/747* | (2015.01) | |
| *A61K 9/00* | (2006.01) | |
| *A61K 9/20* | (2006.01) | |
| *A61K 9/48* | (2006.01) | |
| *A61K 47/26* | (2006.01) | |
| *A61K 47/38* | (2006.01) | |

(52) U.S. Cl.
CPC .......... *A61K 35/747* (2013.01); *A61K 9/0014* (2013.01); *A61K 9/20* (2013.01); *A61K 9/48* (2013.01); *A61K 47/26* (2013.01); *A61K 47/38* (2013.01)

(58) Field of Classification Search
CPC .................................................... A61K 35/747
See application file for complete search history.

(56) References Cited

U.S. PATENT DOCUMENTS 11,446,343 B2 * 9/2022 Kort ......................... C12N 1/20

FOREIGN PATENT DOCUMENTS

| EP | 2428214 A1 | 3/2012 |
| EP | 3040413 A1 | 7/2016 |
| WO | 2006045475 A1 | 5/2006 |
| WO | 2016100086 A1 | 6/2016 |

OTHER PUBLICATIONS

Ngugi et al. "Effects of Bacterial Vaginosis-Associated Bacteria and Sexual Intercourse on Vaginal Colonization With the Probiotic Lactobacillus crispatus CTV-05." Sexually Transmitted Diseases 38.11 (2011): 1020. doi: 10.1097/OLQ.0b013e3182267ac4. 17 pages.
International Search Report and Written Opinion in corresponding International Patent Application No. PCT/NL2018/050479 mailed Oct. 4, 2018. 11 pages.
Nunn et al., "Unraveling the Dynamics of the Human Vaginal Microbiome", Yale Journal of Biology and Medicine 89 (2016), pp. 331-337. 7 pages.
Van der Veer et al., "Comparative genomics of human Lactobacillus crispatus isolates reveals genes for glycosylation and glycogen degradation: implications for in vivo dominance of the vaginal microbiota", Microbiome 7:49, pp. 1-14, 2019.

* cited by examiner

*Primary Examiner* — Albert M Navarro
(74) *Attorney, Agent, or Firm* — Leason Ellis LLP

(57) ABSTRACT

The present invention relates to a mixture of strains of *Lactobacillus crispatus*, which mixture comprises strains that have a different carbohydrate degradation profile, comprising at least one strain of *L. crispatus* that is able to degrade glycogen, and at least one strain of *L. crispatus* that is able to degrade lactose. Such a mixture is of use in the treatment or prevention of bacterial vaginosis, preferably to decrease recurrence of bacterial vaginosis after treatment with antibiotics.

14 Claims, 9 Drawing Sheets

Figure 1:
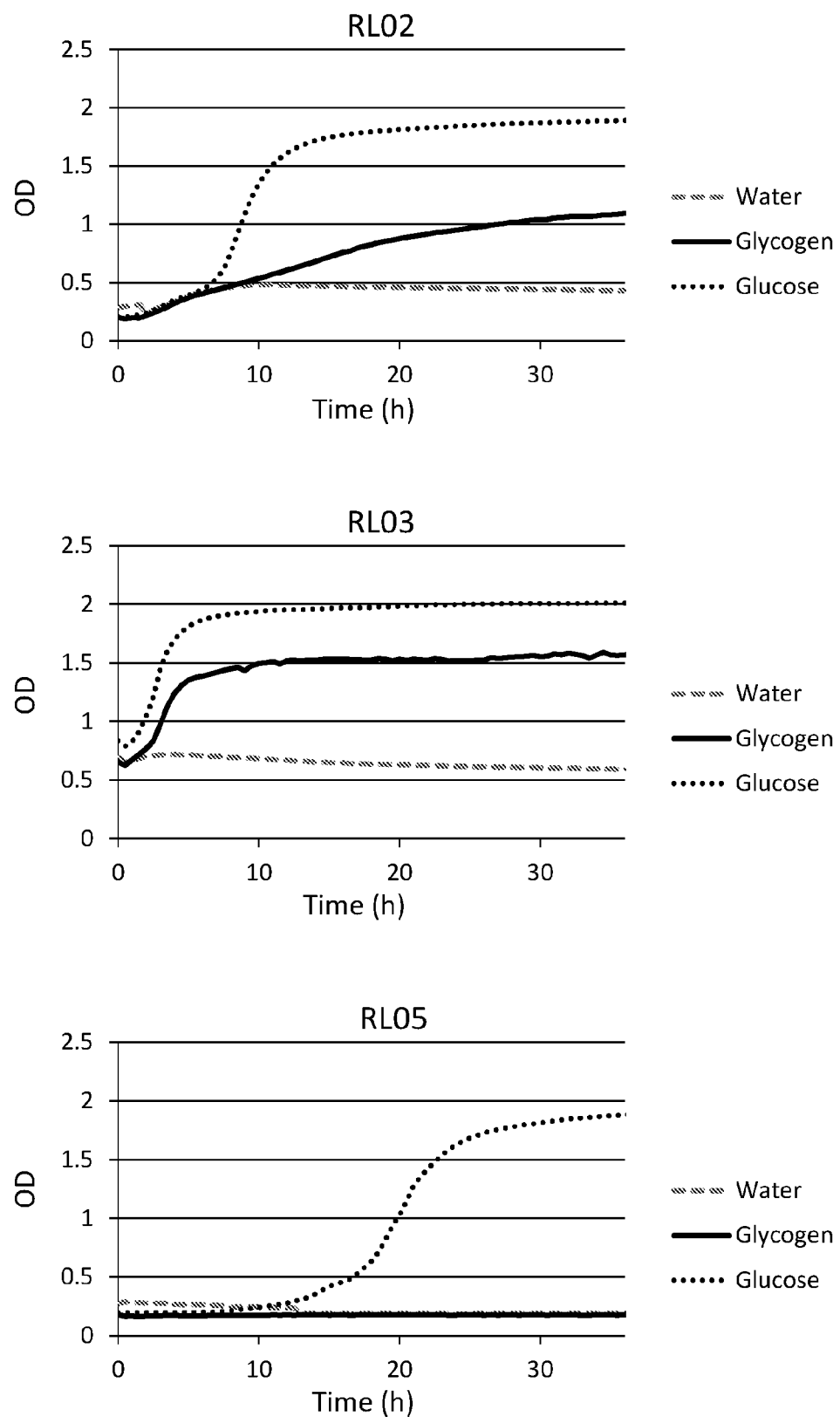

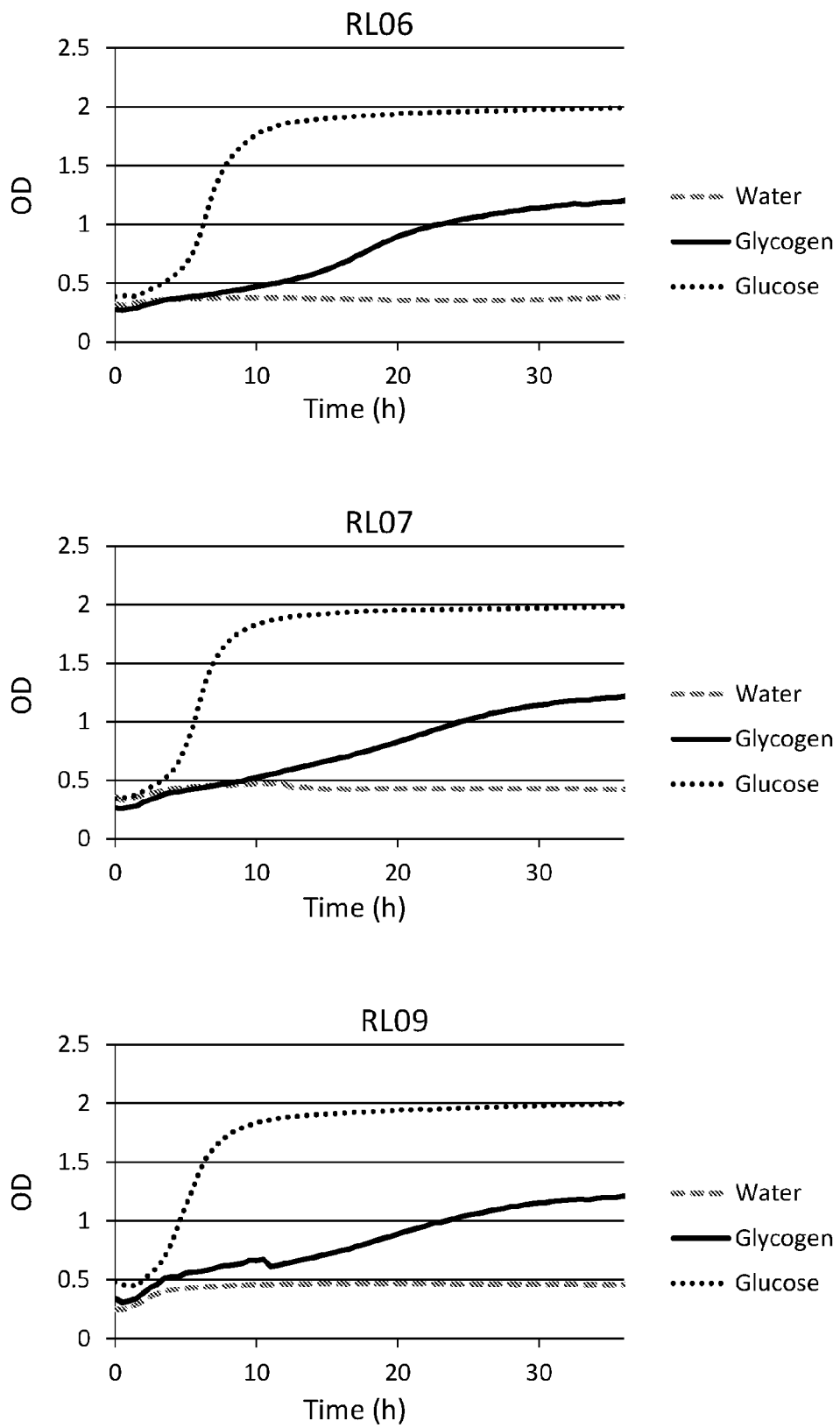
Fig. 1, Cont'd

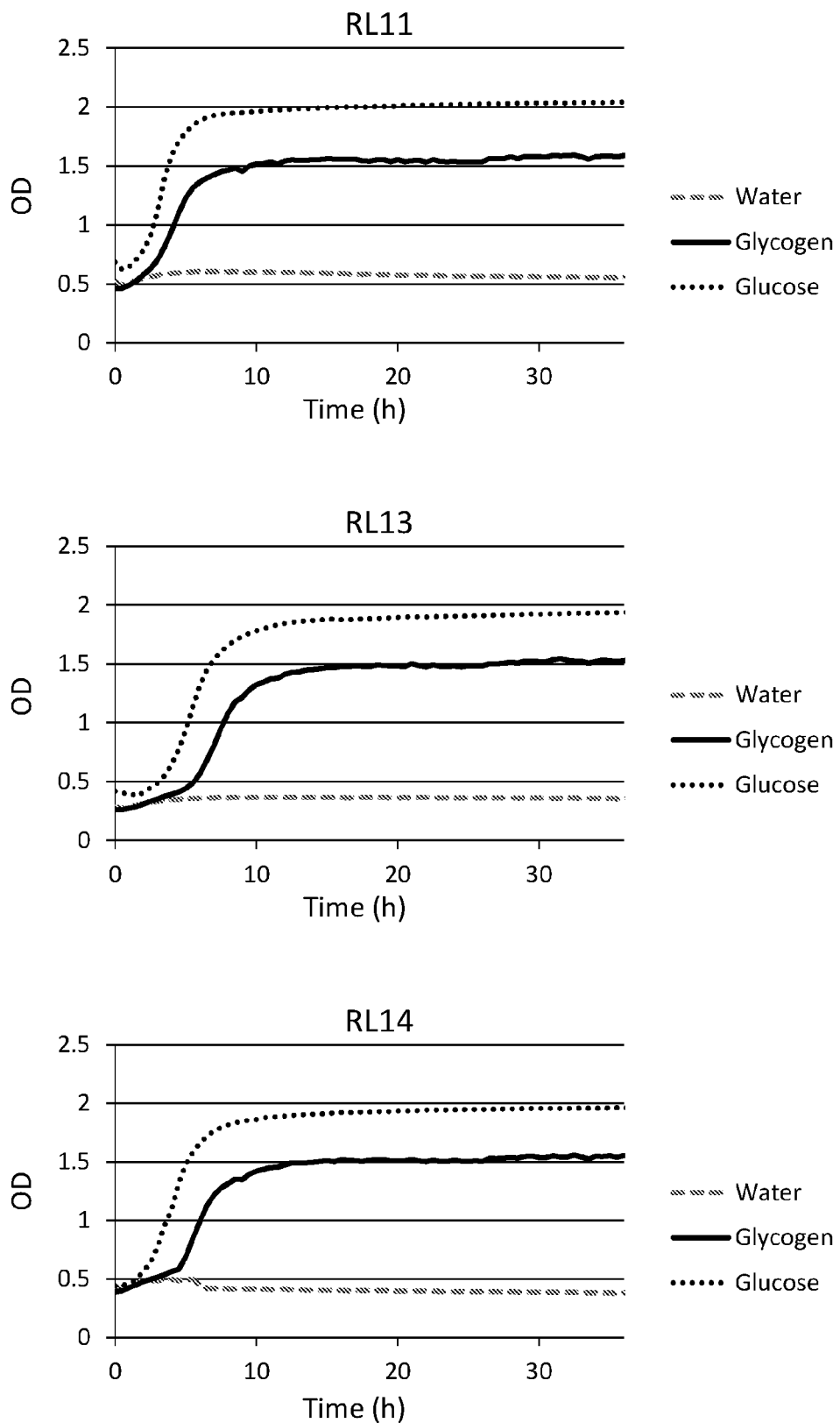
Fig. 1, Cont'd

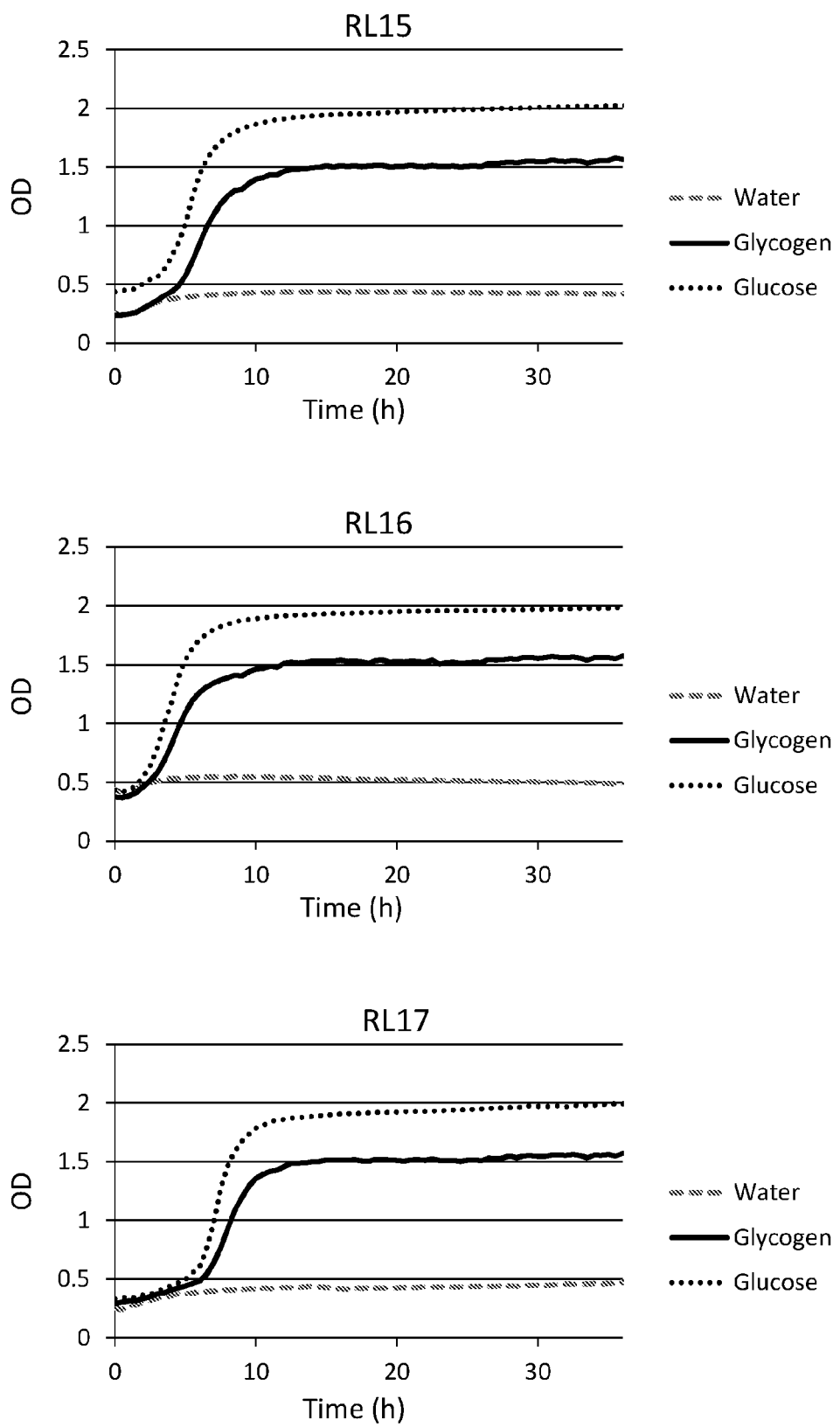
Fig. 1, Cont'd

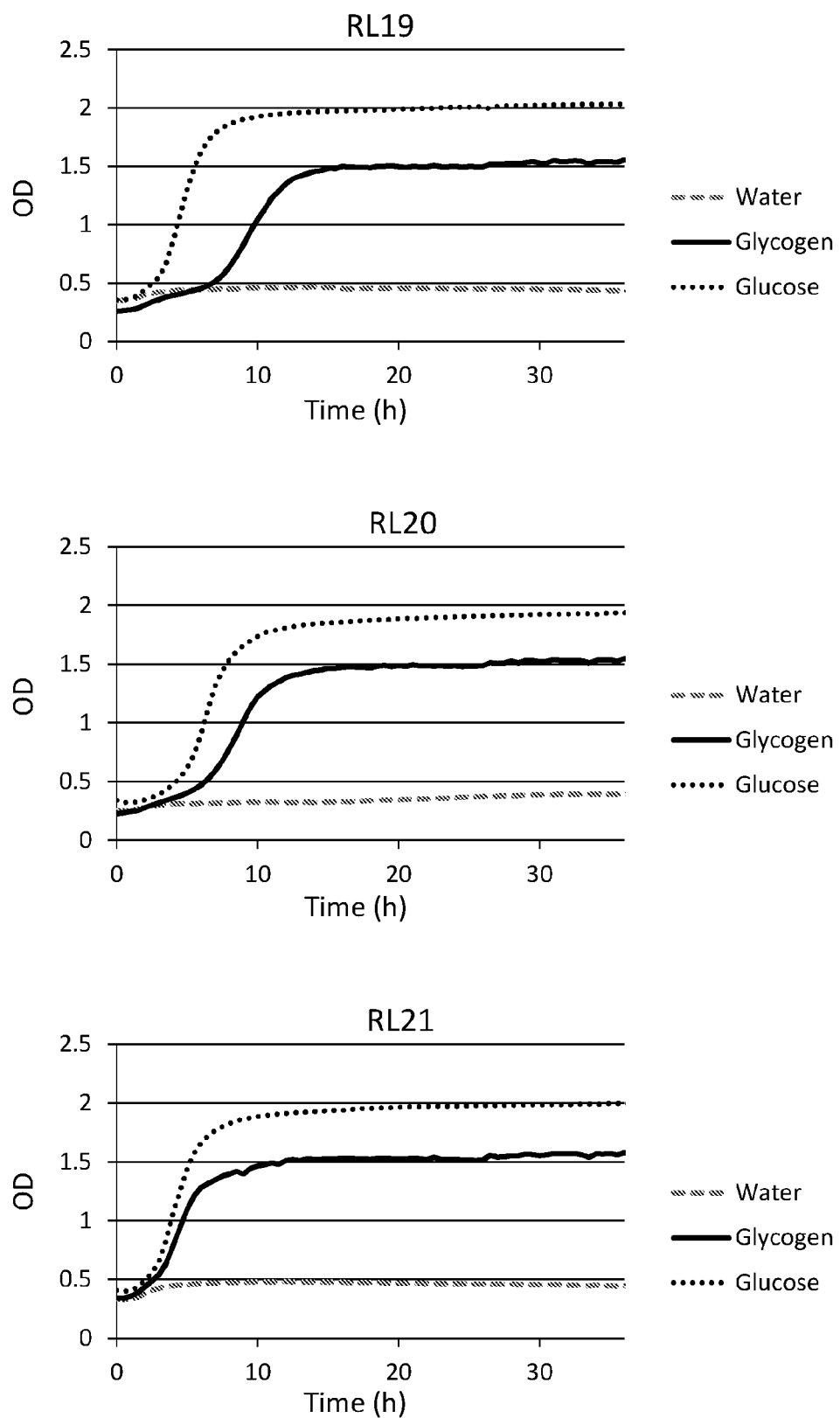
Fig. 1, Cont'd

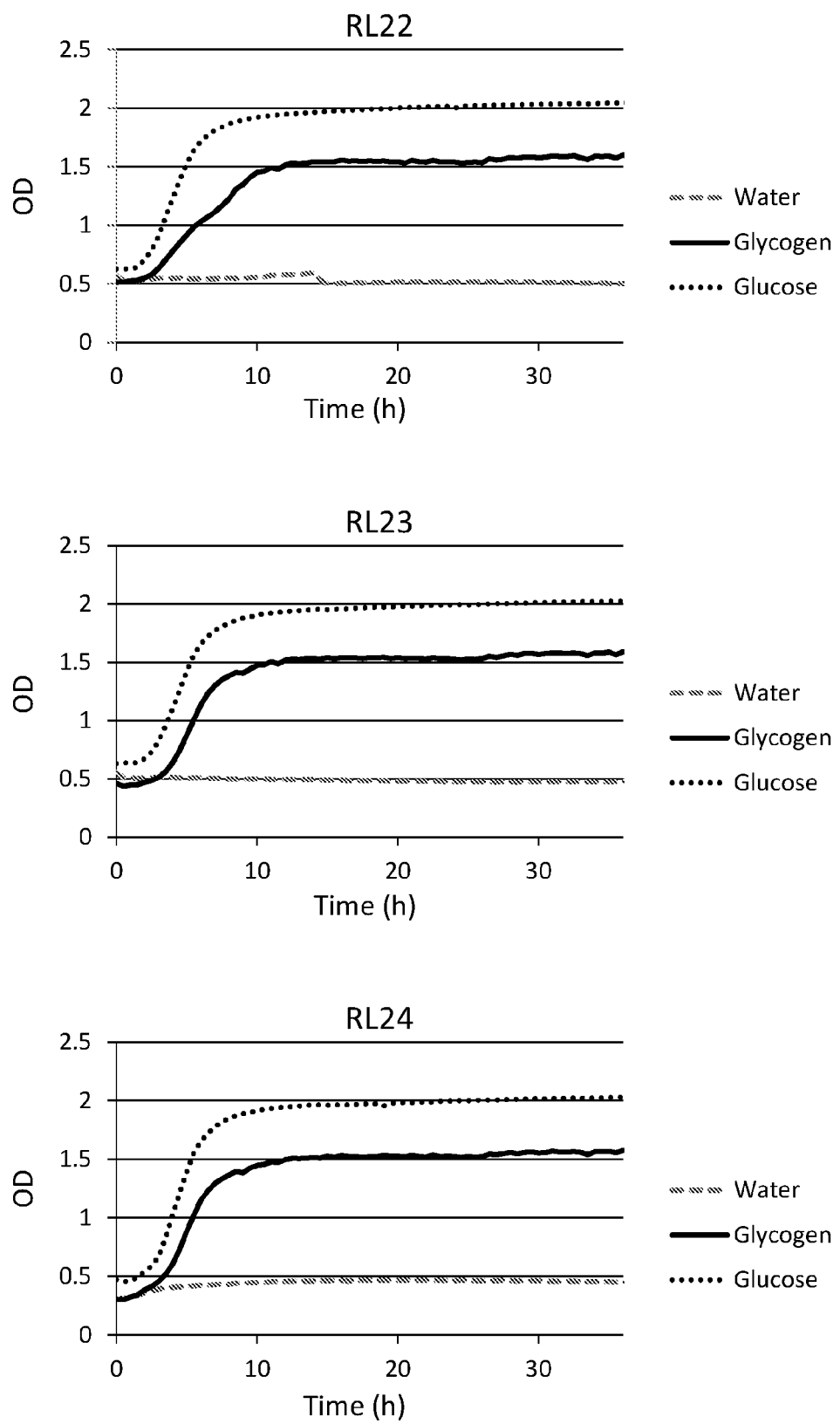
Fig. 1, Cont'd

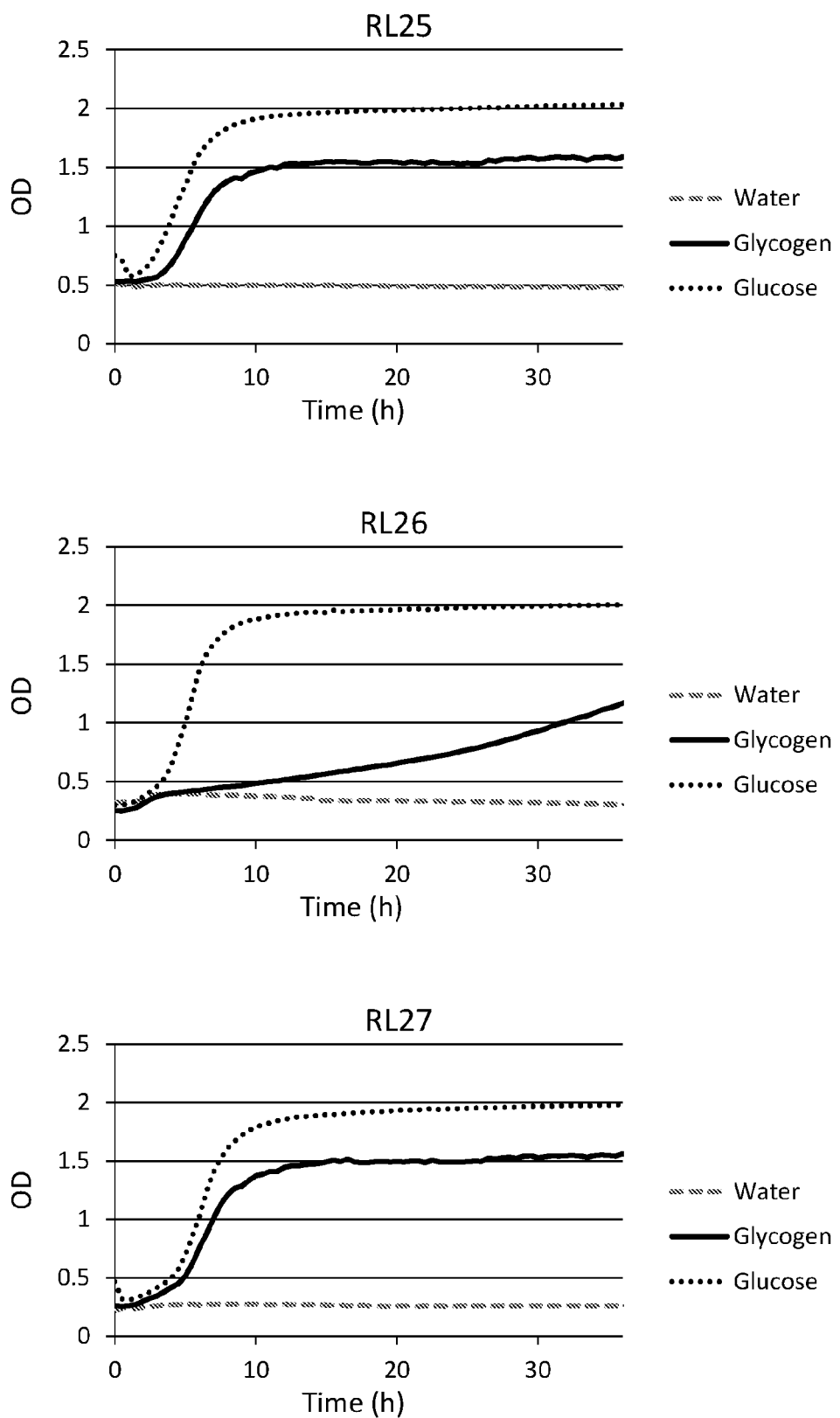
Fig. 1, Cont'd

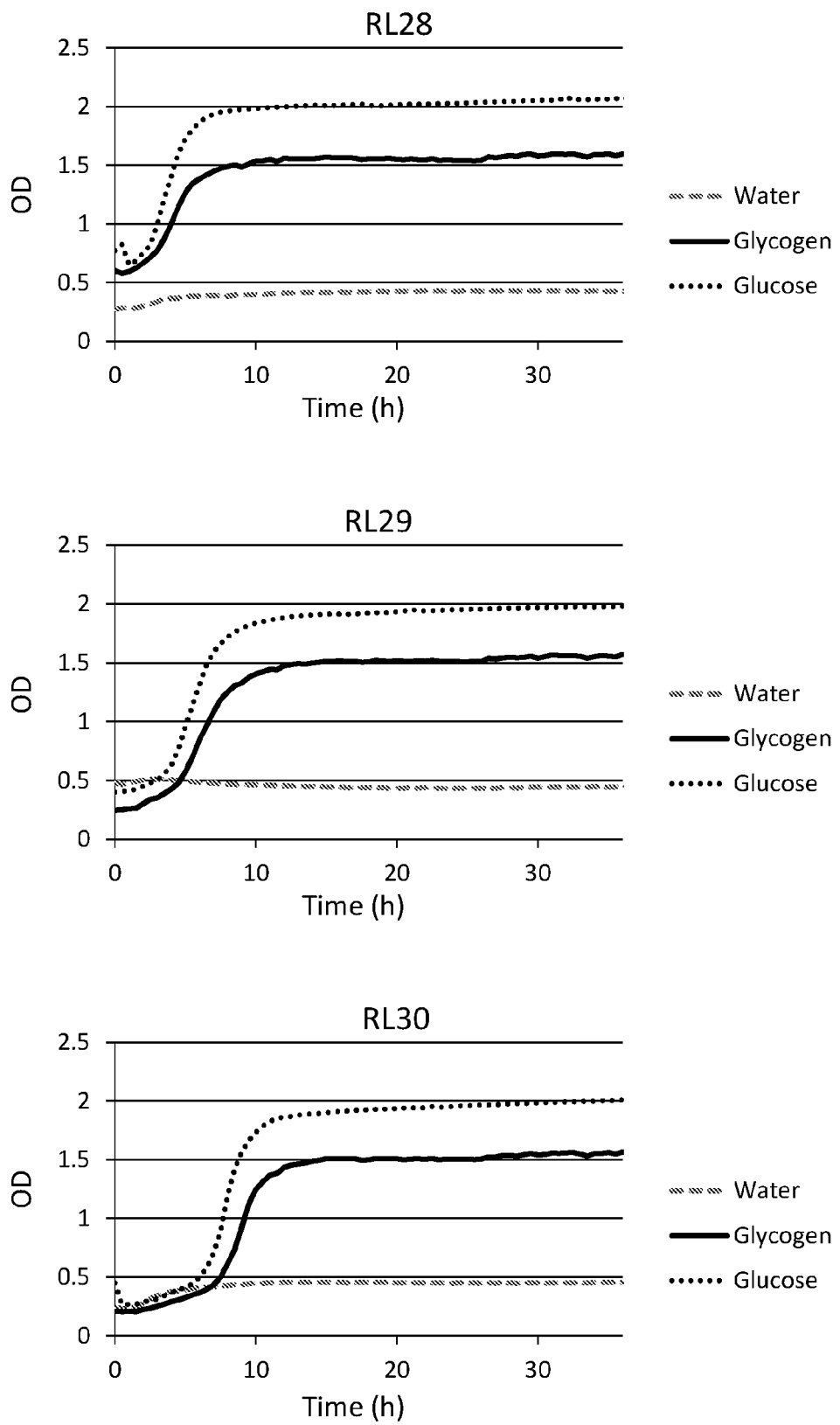
Fig. 1, Cont'd

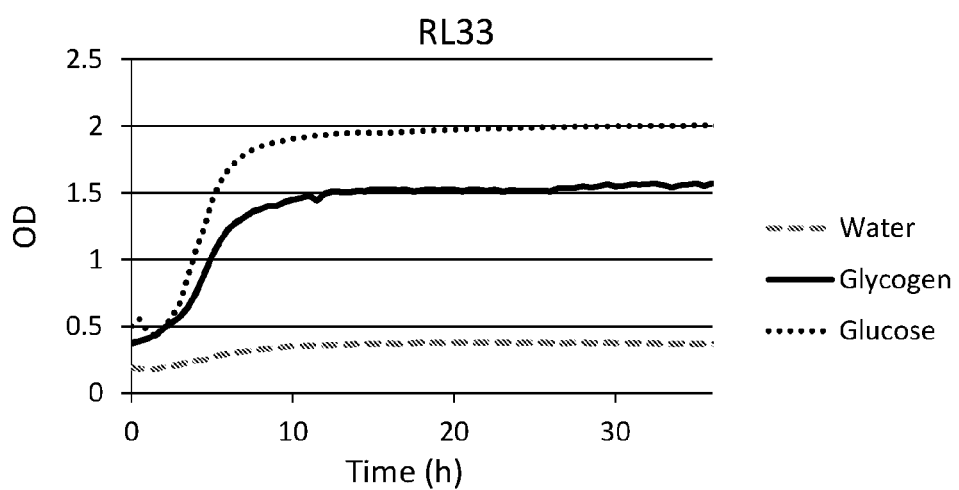
Fig. 1, Cont'd

PROBIOTIC COMPOSITION FOR PREVENTION OF BACTERIAL VAGINOSIS

CROSS-REFERENCE TO RELATED PATENT APPLICATIONS

This application is a Continuation Application of U.S. patent application Ser. No. 16/628,762, filed Jan. 6, 2020, which is a National Stage Application under 35 U.S.C. § 371 of International Patent Application No. PCT/NL2018/050479, filed Jul. 12, 2018, which claims the benefit of priority of European Patent Application number 17181005.4 filed Jul. 12, 2017, all of which are incorporated by reference in their entireties.

FIELD OF THE INVENTION

The invention relates to the fields of medicine, bacteriology and health science. More particular, the invention relates to the field of bacterial-based treatment by administration of bacterial cultures.

BACKGROUND OF THE INVENTION

Probiotics, are defined by the FAO and the WHO as living microorganisms which, when administered in adequate amounts, confer a beneficial health effect on the host. Although in most cases administration is given orally, the definition does not exclude other modes of administration. Addition of probiotic bacteria to the diet is an approach for increasing the health of the individual human or animal by promoting the presence of beneficial bacteria in the intestine.

Multiple microorganisms exist in a healthy woman's vagina, and form a vaginal micro-ecosystem of mutual restriction, mutual coordination and dynamic equilibrium with the host and the environment. In the vagina the most abundant bacterial genus is that of *Lactobacillus* (dominated by *L. crispatus, L. gasseri, L. iners, L. jensenii* and/or *L. vaginalis*), which are responsible for the lactic acid production, which is characteristic for the vaginal environment. Other lactic acid-producing bacteria that contribute to vaginal acid production by fermentation, i.e. species from the genera *Atopobium, Leptotrichia, Leuconostoc, Megasphaera, Pediococcus, Streptococcus* and *Weissella* may also be present. These Lactobacilli can protect the vagina under normal circumstances, while a dysbiosis of the *Lactobacillus*-predominant vaginal micro-ecosystem can cause vaginitis. However, also several anaerobic bacterial species are frequently found in the vagina, such as the Grampositive cocci: *Atopobium vaginae, Peptostreptococcus* spp., *Staphylococcus* spp., *Streptococcus* spp., and *Bacteroides* spp., *Fusobacterium* spp., *Gardnerella vaginalis, Mobiluncus, Prevotella* spp., and Gram-negative enteric organisms, such as *Escherichia coli*.

Bacterial vaginosis is an aberrant state of the vaginal microbiota, which is characterized by an increase of the vaginal pH, a reduction of *Lactobacillus* spp., and an increased diversity of vaginal anaerobic bacteria and which thus may be characterized as an example of dysbiosis. Occurrence of bacterial vaginosis (BV) is caused by massive propagation of other conditional pathogenic microorganisms such as *Gardnerella vaginalis*, various anaerobic bacteria, *Campylobacter* and the like due to vaginal dysbacteriosis and reduction of Lactobacilli of the host per se.

Bacterial vaginosis is the most common vaginal infection among women during reproductive age and it is also frequent among pregnant women. Bacterial vaginosis represents more than 60% of the overall vaginal infections. The National Center for Health Statistics—National Health and Nutrition Survey (NHANES) in a survey carried out on more than 12.000 women in USA on 2001-2004 showed that the prevalence of bacterial vaginosis was 29.2%, but only 15.7% was symptomatic. A good percentage of vaginosis is thus asymptomatic, namely does not lead to symptoms typical of vaginal inflammations such as itching, burning and pain during sexual activity. Many of them, inter alia, do not either cause irritations, redness or swelling but, in any case, they cause an increase of vaginal discharges, with white or grayish secretions, characterized by a bad smell. Due to the fact that vaginal discharges substantially change depending on the menstrual cycle stage, the woman is often unable to understand that there is an ongoing infection and vaginosis is not diagnosed. The non-treatment of a vaginosis can lead to the onset of even severe vaginitis and infections, mainly in particularly sensitive subjects. Furthermore, it can contribute in transmitting infections through the sexual activity.

Although the application of antibiotic treatment may respite the symptoms of the BV, it even further reduces the amount of Lactobacilli, exacerbating vaginal micro-ecology dysbiosis and therefore causing repeated recurrence of BV. How to control the recurrence and how to thoroughly cure the bacterial vaginosis are problematic issues. Bacterial vaginosis is associated with adverse pregnancy outcomes, upper genital tract infections and increased risk of sexual transmitted diseases.

Next to antibiotics, probiotica, however, are also known for the treatment of bacterial vaginosis. Normally probiotics are provided by culturing a specific micro-organism or, at best, a mixture of specific micro-organisms. Several of these products have been suggested in the literature (e.g. US 2002/044926, US 2012/189,599, US 2016/074,440, US 2016/184,372, US 2017/020,934, WO 2017/001440 and reviewed in Falagas, M. et al., Clin. Microbiol. Infect, 2007, 13 (7): 657-664). If these are administered to combat conditions of dysbiosis, such as bacterial vaginosis, these probiotics are deemed able to 'normalise' the microbiota.

Recently, it has been found that it is also feasible—and probably more preferable, to provide one (or more) of the patient's own species of micro-organisms. Such a scheme would fit into today's development of 'personalised therapeutics'. One example has been described in US 2003/118,571 in which a micro-organism is isolated from a human sample and cultured and, after sufficient culturing, supplied to that same human. In that same document it has also been proposed that microbiota restoration, especially urogenital microbiota restoration can be achieved with a bacterial species that has been isolated from that patient. For this, when the patient in need of microbiota restoration or maintenance is healthy, urogenital organisms are recovered, cultured and the main healthy species isolated and stored. If and when the person has a depleted urogenital microbiota at some later point in his/her life, such as during pregnancy or during a urogenital infection, the originally isolated organisms are cultured, and re-implanted vaginally or re-administered orally.

Nevertheless these recent developments, there is still need for a probiotic medicament for the prevention and treatment of bacterial vaginosis.

SUMMARY OF THE INVENTION

The inventors now found that the vaginal species of *Lactobacillus crispatus* in fact is composed of a lot of strains of *L. crispatus* that vary with respect to their carbohydrate substrate specificity. The invention thus comprises a mixture of strains of *Lactobacillus crispatus*, which mixture comprises strains that have a different carbohydrate degradation profile, further comprising at least one strain of *L. crispatus* that is able to degrade glycogen, and at least one strain of *L. crispatus* that is able to degrade lactose. Preferably, said strains have been isolated from a woman without bacterial vaginosis. In a preferred embodiment said mixture in total comprises 4 or more strains of *L. crispatus* that differ from each other on basis of their carbohydrate degradation profile, preferably comprising at least 2 strains that are able to degrade glycogen and at least 2 strains that are able to degrade lactose.

A further preferred embodiment is a mixture according to the invention comprising at least one glycogen degrading strain chosen from CBS 142868, CBS 142871 and CBS 142874, as deposited with the Westerdijk Fungal Biodiversity Institute on Jul. 4, 2017 and CBS 142869 as deposited with the Westerdijk Fungal Biodiversity Institute on Jun. 9, 2017, and at least one lactose degrading strain chosen from CBS 142870, CBS 142871, CBS 142872, CBS 142873 and CBS 142874 as deposited with the Westerdijk Fungal Biodiversity Institute on Jul. 4, 2017. Most preferred is an embodiment in which at least six of these deposited strains mentioned above are comprised.

Also part of the invention is a probiotic composition comprising the mixture according to the invention and lactose. Preferably, said composition additionally comprises glycogen, and more preferably additionally comprises a carbohydrate mixture comprising two or more carbohydrates selected from the group of glycogen, galactose, glucose, lactulose, mannose, n-acetylglucosamine, cellobiose, maltose, mannose, mannitol, raffinose, trehalose, saccharose, starch, amygdalin, arbutin, salicin and esculin.

In a further preferred embodiment, the invention comprises a mixture as defined above, or a composition as defined above for use in therapy. Said use is preferably the treatment or prevention of bacterial vaginosis, more preferably to decrease recurrence of bacterial vaginosis after treatment with antibiotics. Preferably said treatment is topical treatment Also part of the invention is a method for the treatment or prevention of bacterial vaginosis, preferably to decrease recurrence of bacterial vaginosis after treatment with antibiotics, comprising topical administration of a mixture as defined above or a composition as defined above. Preferably, in said method the prevention or treatment of bacterial vaginosis comprises first treatment with an antibiotic compound, followed by administration of a mixture according to the invention or a composition according to the invention Also comprised in the invention is the use of a mixture according to the invention or a composition according to the invention for the manufacture of a medicament for topical treatment of bacterial vaginosis, preferably to decrease recurrence of bacterial vaginosis after treatment with antibiotics.

Also part of the invention is a vaginal capsule or vaginal tablet comprising a mixture according to the invention or a composition according to the invention.

LEGENDS TO THE FIGURES

FIG. 1 shows the substrate consumption and growth of various *L. crispatus* strains isolated from both healthy women and women with vaginal dysbiosis (in total 25). In all cases glucose is the substrate on which the best growth is observed, followed by glycogen as substrate. The third substrate (water) was used as negative control and indeed no growth was observed on this substrate.

DETAILED DESCRIPTION

Definitions

The term "probiotic composition" as used herein refers to a composition comprising one or more probiotic organisms and one or more acceptable excipients suitable for application to a mammal, preferably a human. It will be appreciated that acceptable excipients will be well known to the person skilled in the art of probiotic composition preparation. Examples of such acceptable excipients for oral administration of the probiotic composition include: sugars such as sucrose, isomerized sugar, glucose, fructose, maltose, mannose, sorbose, rhamnose, arabinose, palatinose, trehalose, lactose, cellobiose, melibiose and xylose; sugar alcohols such as sorbitol, mannitol, xylitol, inositol, erythritol, lactitol, palatinol, reduced glutinous starch syrup and reduced glutinous maltose syrup; polysaccharides as maltodextrins, inulins, starches like maize starch, rice starch, potato starch and wheat starch, glucosides like amygdalin, erbutin, esculin, salicin, N-acetylglucosamine and the like, emulsifiers such as sucrose esters of fatty acid, glycerin esters of fatty acid and lecithin; thickeners (stabilizers) such as carrageenan, xanthan gum, guar gum, pectin and locust bean gum; acidifiers such as citric acid, lactic acid and malic acid; fruit juices such as lemon juice, orange juice and berry juice; vitamins such as vitamin A, vitamin B, vitamin C, vitamin D and vitamin E; and minerals such as calcium, iron, manganese and zinc. For topical administration of a probiotic composition the composition can additionally or alternatively comprise polymers, such as natural polymers including proteins such as zein, modified zein, casein, gelatin, gluten, serum albumin, and collagen, polysaccharides such as cellulose, dextrans, and polyhyaluronic acid, or synthetic polymers including polyphosphazenes, poly(vinyl alcohols), polyamides, polycarbonates, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Examples of suitable polyacrylates include poly(methyl methacrylate), poly(ethyl methacrylate), poly (butyl methacrylate), poly(isobutyl methacrylate), poly (hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate). Synthetically modified natural polymers include cellulose derivatives such as alkyl celluloses, hydroxyalkyl celluloses, cellulose ethers, cellulose esters, and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. Also usable are degradable polymers, such as polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers. It is also possible that the probiotic is administered in the form of a hydrogel. Suitable hydrogels can be formed from synthetic polymers such as polyethylene glycol, polyethylene oxide, polyvinyl alcohol, polyvinyl pyrrolidone, polyacrylates, poly (ethylene terephthalate), poly(vinyl acetate), and copolymers and blends thereof, as well as natural polymers such as cellulose and alginate, as described above.

Probiotic compositions for topical administration may be applied in the form of crèmes or ointments. As such they will ideally comprise an oily substance originating from vegetable, marine or animal sources. Suitable liquid oil includes saturated, unsaturated or polyunsaturated oils. By way of example, the unsaturated oil may be olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils or mixtures thereof, in any proportion. These crèmes or ointments may further comprise poly-unsaturated fatty acids. In one or more embodiments, said unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Such unsaturated fatty acids are known for their skin-conditioning effect, which contribute to the therapeutic benefit of the composition. Thus, the composition can include at least 6% of an oil selected from omega-3 oil, omega-6 oil, and mixtures thereof. Also usable are the essential oils, which are also considered therapeutically active oils, which contain active biologically occurring molecules and, upon topical application, exert a therapeutic effect, which is conceivably synergistic to the beneficial effect of the probiotic mixture in the composition. Another class of therapeutically active oils includes liquid hydrophobic plant-derived oils, which are known to possess therapeutic benefits when applied topically. Silicone oils also may be used and are desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. These are chosen from cyclic or linear polydimethylsiloxanes containing from about 3 to about 9, preferably from about 4 to about 5, silicon atoms. Volatile silicones such as cyclomethicones can also be used. Silicone oils are also considered therapeutically active oils, due to their barrier retaining and protective properties.

For vaginal application the probiotic composition may be in the form of a vaginal capsule or vaginal tablet. The term "capsule" refers to a hard shell pharmaceutical capsule. The capsule consists of a body and cap and may comprise a fill formulation containing the probiotic composition. Capsules suitable for use according to the invention include, without limitation NPcaps® available from Capsugel which contain pullulan, carageenan and potassium chloride, as well as capsules described in U.S. Pat. No. 8,105,625 and US Patent Application Publication No. 2005/0249676. In one aspect, capsules for use according to the invention comprise pullulan with a molecular weight between about 50 to 500 kDa, between 100 to 400 kDa, between about 150 to 300 kDa and preferably between about 180 and 250 kDa. In another aspect, capsules for use according to the invention comprise pullulan from about 50% to about 100% by weight (unfilled capsule). In other aspects, the capsules comprise about 60 to 90 or 70 to 90, or 80 to 90 wt % pullulan. Preferably the capsules comprise about 85 to 90 wt % pullulan.

Capsules for use according to the invention may further comprise (in addition to pullulan) one or more gelling agents (e.g. hydrocolloids or polysaccharides such as alginates, agar gum, guar gum, carob, carrageenan, tara gum, gum arabic, pectin, xanthan and the like); salts comprising cations such as K, Li, Na, NH4, Ca, Mg; and/or surfactants such as sodium lauryl sulphate, dioctyl sodium sulfosuccinate, benzalkonium chloride, benzethonium chloride, cetrimide, fatty acid sugar esters, glycerl monooleate, polyoxyethylene sorbitan fatty acid esters, polyvinylalcohol, dimethylpolysiloxan, sorbitan esters or lecithin, as described in US Patent Application Publication No. 2005/0249676.

Capsules for use according to the invention may further comprise one or more plasticizing agents (e.g. glycerol, propylene glycol, polyvinyl alcohol, sorbitol, maltitol and the like); dissolution enhancing agents (e.g. maltose, lactose, sorbitol, mannitol, xylitol, maltitol and the like); strengthening agents (e.g. polydextrose, cellulose, maltodextrin, gelatin, gums and the like); colorants, and/or opacifiers as described in U.S. Pat. No. 8,105,625. In a preferred embodiment, the capsule comprises pullulan in an amount of 85% to 90% by weight, potassium chloride in an amount of 1.0% to 1.5% by weight, carrageenan in an amount of 0.1% to 0.4% by weight, one or more surfactants in an amount of 0.1% to 0.2% by weight and water in an amount of 10% to 15% by weight.

In a particularly preferred embodiment, the capsule comprises pullulan in an amount of 86.3% by weight, potassium chloride in an amount of 1.32% by weight, carrageenan in an amount of 0.27% by weight, surfactants selected from sugar esters, sorbitan monolaurate and combinations thereof in an amount of 0.15% by weight and water in an amount of 12% by weight.

The term "dysbiosis" or "dysbiotic condition" is defined as a state in which the microbiota produces harmful effects via (a) qualitative and quantitative changes in the content or amount of the microbiota itself, (b) changes in their metabolic activities; and/or (c) changes in their local distribution. Specifically, dysbiosis of the vagina is defined as an aberration of the healthy state. A healthy state is defined in this case as a condition with a relatively low susceptibility to sexually transmitted diseases. It has been widely accepted that the activity of *Lactobacillus* spp. contributes to maintain this low susceptibility through the protection of the vaginal environment against pathogens by the production of lactic acid, resulting in a low pH. Hence, vaginal dysbiosis is, amongst others, characterized by the presence of a relative high pH.

The term "microbiota" as used herein denominates the community of commensal microorganisms that colonise (parts of) an organ of the host, such as the vagina, together with the food-ingested, or transient microorganisms. However, these transient microbiota are not regarded as part of the so-called 'indigenous microbiota'. "Epithelium" or "epithelial cell or tissue" as used herein is one of the four basic types of animal tissue, along with connective tissue, muscle tissue and nervous tissue. Epithelial tissues line the cavities and surfaces of structures throughout the body, and also form many glands. Functions of epithelial cells include secretion, selective absorption, protection, transcellular transport and detection of sensation.

"Mucosa" as used herein is the term used to indicate a mucous membrane. Mucus (adjectival form: "mucous") is a slippery secretion produced by, and covering, mucous membranes. Mucous fluid is typically produced from cells found in mucous glands. Mucous cells secrete products that are rich in glycoproteins and water. Mucous fluid may also originate from mixed glands, which contain both serous and mucous cells. It is a viscous colloid containing antiseptic enzymes (such as lysozyme), immunoglobulins, inorganic salts, proteins such as lactoferrin, and glycoproteins known as mucins that are produced by goblet cells in the mucous membranes and submucosal glands. This mucus serves to protect epithelial cells (the lining of the tubes) in the respiratory, gastrointestinal, urogenital, visual, and auditory systems in mammals.

In a healthy human or animal, the internal tissues, e.g. blood, brain, muscle, etc., are normally free of microorganisms. However, the surface tissues, i.e., skin and mucous membranes, are constantly in contact with environmental organisms and become readily colonized by various microbial species. The mixture of organisms regularly found at any anatomical site is referred to as the normal flora, or preferably "indigenous microbiota". The normal flora of humans consists of a few eukaryotic fungi and protists, but bacteria are the most numerous and obvious microbial components of the normal flora. Although humans are exposed to a wide variety of microbes throughout their lives, only a limited number of species are able to permanently colonize the various body sites available, and each body site harbours a microbial community comprised of certain characteristic species.

Residents of a body site should be able to grow and reproduce under the conditions operating at the site, whereas organisms that cannot do so, are regarded as transients.

DETAILED DESCRIPTION OF THE EMBODIMENTS OF THE INVENTION

In case a subject suffers a condition of vaginal dysbiosis the therapy should be pointed at the recovery of the local microbiota balance. Known probiotic therapies as reviewed by Falagas et al. (supra) centre around administration of cultured microbiological species, where a single microorganism is prepared to restore the balance. In some cases probiotic mixtures are available, but mostly monocultures have been applied. For *Lactobacillus crispatus* a therapeutic use has been demonstrated for the CTV-05 strain (Antonia, M. et al., J. Infect. Dis. 199:1506-1513, 2009). When mixtures have been applied, those mixtures generally consisted of different species of bacteria of which also monocultures are provided. In this respect combinations of *Lactobacillus rhamnosus* DSM 14870 and *Lactobacillus gasseri* DSM 14869 (Ecovag®) and *Lactobacillus rhamnosus* GR-1® and *Lactobacillus reuteri* RC-14® (Optibac®) are commercially available.

It appears, however, that there is quite a large variation from subject to subject in the composition of the microbiota. The individualisation of microbiota (in this case intestinal microbiota) has been evidenced in several recent studies (e.g. Faith, J. J. et al . . . , Science 341:1237439). In these studies it appeared that strains, defined as isolates sharing >96% of their genome content, were maintained over time within an individual and between family members but not between unrelated individuals.

Such a variation is not only to be found between subjects, but also the same subject can experience large variations in the microbiota over time. This can be demonstrated with vaginal microbiota as an example. The vagina, which is sterile at birth, is colonised by maternal Lactobacilli within a few days. This concurs with the theory that normal human microbiota derive mainly from the mother. In most cases, this microbiota will remain prevalent throughout life; in the vagina, its presence will be mainly influenced by hormone levels. The presence of Lactobacilli is strongly influenced by the availability of glycogen, the levels of which are regulated by the oestrogens. A few weeks after birth there is a reduction in the *Lactobacillus* population, to the advantage of coagulase-negative staphylococci, streptococci, *Escherichia coli* and other intestinal bacteria. Later, at puberty, the ideal conditions for multiplication of Lactobacilli are restored (increased oestrogen levels and thickening of the vaginal mucosa); Lactobacilli thus become the dominant vaginal microbiota in adult women. During this period the microbial population in a vaginal secretion amounts to approx. 107-108 CFU/g. This microbial population remains substantially unchanged until the menopause, when it is replaced by a more diverse microbiota, not unlike that of the prepuberal period, but with a considerable presence of *mycoplasma* and, to a lesser extent, anaerobic bacteria (e.g. *Gardnerella vaginalis*).

Various studies have attempted to characterise the vaginal Lactobacilli at species level. These studies demonstrate that there is a geographical difference in the composition of the vaginal microbiota. However, bacteria belonging to what is often called the *Lactobacillus acidophilus* complex seem to constitute the dominant species at childbearing age.

It now has been found that there is a large variation of strains within the *Lactobacillus crispatus* species, where these strains are unique with respect to their carbohydrate substrate profile (see Table 1). This is of interest in the case of bacterial vaginosis because the cause of the occurrence of the condition may reside in the (lack of) availability of the substrate for the healthy bacterial strains/species. As has been shown in literature (Srinivasan, S. et al., mBio 6 (2): e00204-15. doi: 10.1128/mBio.00204-15) the metabolic surroundings in the vagina showed enormous changes under bacterial vaginosis conditions. This also means that success of the application of probiotics for the prevention or treatment of BV is lowered when species are provided that can not grow well on the available substrate.

Accordingly, the invention comprises a probiotic composition comprising a mixture of *Lactobacillus crispatus* strains, which mixture comprises strains that have a different carbohydrate degradation profile, comprising at least one strain of *L. crispatus* that is able to degrade glycogen, and at least one strain of *L. crispatus* that is able to degrade lactose. Glycogen is one of the main substrates that is found in the healthy vagina. Proof that glycogen promotes *Lactobacillus* growth and maintenance in the vagina has been given in the recent literature (Mirmonsef, P. et al., PLOS ONE 9 (7): e102467. doi: 10.1371/journal.pone.0102467). Lactose, although not or hardly present naturally in the vagina, is commonly used in vaginal treatments, such as vaginal douches. Also, a commercially obtainable vaginal tablet containing lactose (LadyBalance™) has been shown to be effective in the treatment and prevention of BV (Emery, S. J. et al., Sex Transm. Infect. 88: A27, 2012). Next to glycogen and lactose, also mannose, glucose and glucosamine are important carbohydrates that function as a substrate in the healthy vagina (see also: Rajan, N. et al., Infect. Immun. 1999, 67 (10): 5027-5032).

The carbohydrate degradation profile as used in the present invention can be assessed by culturing a bacterial isolate strain on a variety of carbohydrate substrates, such as the API CH50 test by using API 50 CH carbohydrate fermentation strips (bioMérieux, Inc., Marcy l'Etoile, France). Such a test system is advantageously used to characterize *Lactobacillus* bacteria (see Boyd, M. A. et al., J Clin Microbiol 43 (10): 5309-5311, 2005). A different carbohydrate degradation profile of two *L. crispatus* strains means that the score in this API 50 CH test differs between said two strains. Examples of strains having different profiles may be found in Table 1.

Preferably the strains that are present in the mixture are (originally) derived from the microbiota of healthy women, i.e. women that do not have bacterial vaginosis. In order to be effective it is preferred to have more than two strains in the mixture and good results have been obtained when using four strains or more. Although it is possible to make new isolates from freshly obtained samples and culturing the isolated strains, it is preferred to use the bacterial strains that have been tested for the present invention and that have been deposited with the Westerdijk Fungal Biodiversity Institute, having an address of Uppsalalaan 8, P.O. Box 85167, 3508 AD Utrecht, The Netherlands, on Jun. 9, 2017, under number CBS 142869, and on Jul. 4, 2017 under numbers CBS 142868, CBS 142870, CBS 142871, CBS 142872, CBS 142873 and CBS 142874. These strains are the strains represented in Table 1 by the respective identifications: 102_026, 102_003, 102_004, 102_006, 102_011, 102_012 and 102_022. Most preferred are mixtures wherein at least four or more strains are present, which strains are selected from glycogen degrading strains selected from CBS 142868, CBS 142869, CBS 142871 and CBS 142874 and lactose degrading strains selected from CBS 142870, CBS 142871, CBS 142872, CBS 142873 and CBS 142874.

Most preferred is a mixture comprising all of the deposited strains mentioned above.

The invention also comprises a (probiotic) composition comprising a mixture according to the invention and lactose. The lactose in this composition does not only provide a substrate for (at least part of) the bacteria in the mixture, but providing the bacteria in a composition that also contains sugars, such as lactose or other carbohydrates that can serve as substrate for the bacteria, lowers the water activity of the composition and with that improves the shelf life of the composition. Further, the lactose in such a composition would also have a beneficial effect on the vaginal microbiota as has been demonstrated by Boyd et al. (supra) and thus can be used as an additional medicament for the prevention or treatment of bacterial vaginosis.

Further preferred is a composition that also contains glycogen. Although, it has been thought that glycogen can not be used as a substrate by *L. crispatus*, because it apparently lacks the enzymatic machinery for glycogen degradation (Ojala, T. et al., BMC Genomics 15:1070, 2014), our experiments, as described below, show that about 50% of the strains that can be isolated from a healthy vaginal microbiota are able to use glycogen. Also glycogen has been proposed for use in the prevention and treatment of BV: Gynofit® vaginal gel contains lactic acid and glycogen. A study is currently ongoing in Switzerland by the University Hospital Inselspital, Berne and Tentan AG to test the effectiveness of this gel versus antibiotic treatment, ClinicalTrials.gov Identifier: NCT02042287 (see: https://clinicaltrials.gov/ct2/show/NCT02042287). Accordingly, the glycogen in the composition has similar advantages as lactose. It is further preferred that the composition further comprises additional carbohydrates that can function as substrate for the bacteria. A list of possible carbohydrates may be found in Table 1, but also in the definition of the probiotic composition as provided above.

The invention further comprises a mixture according to the invention or a composition comprising said mixture for use in therapy. As will be clear the mixture or a composition containing said mixture can be used as a medicament in the treatment or prevention of bacterial vaginosis. A special form of said medical use is the use in combination or after treatment with an antibiotic. As has been indicated above, the most abundant treatment for BV is the treatment with antibiotics. However, recurrence of BV after completion of such a treatment is a common problem: symptomatic BV persists or recurs at 3 months in up to 50% to 70% of patients, with long-term recurrence approaching 85%. The application of the present mixture or composition together with or after antibiotic treatment will greatly minimize the recurrence of the symptoms of BV and will lead to an improved treatment and/or prevention of BV.

Preferably, the application of the mixture or composition according to the invention is given after the antibiotic treatment.

The type of antibiotic treatment will not actually influence the effectivity of the application of the mixture, although—of course-when the mixture is provided together with the antibiotic treatment it will take longer for the *Lactobacillus* strains in the mixture or composition to colonize the vagina. The antibiotic used may be the antibiotics that are used as the standard treatment for BV, such as metronidazole, clindamycine, amoxicillin or tinidazole, but other antibiotics may also be used. The antibiotic treatment generally is provided as an oral administration, although metronidazole may also be given as a topically applicable gel.

The mixture of the invention or the composition comprising said mixture is preferably given through topical application. For this, it may be in the form of a gel or crème, but preferably it will be provided in the form of a vaginal capsule or vaginal tablet. The skilled person will know how to formulate these topical application formulations.

The invention further comprises the use of the mixture or composition according to the invention for the prevention or treatment or the prevention of recurrence of bacterial vaginosis as indicated above. Also provided in the present invention is the use of the mixture or composition according to the invention for the preparation of a medicament for the prevention or treatment or the prevention of recurrence of bacterial vaginosis.

For the production of sufficient bacteria to produce the mixture of the invention, cultures of the strains as isolated from a healthy woman and/or the bacterial cultures as listed in Table 1 (and deposited under the Budapest Treaty as indicated above) may be produced by culturing the bacteria using methods well known in the art. *Lactobacillus*-MRS Agar [introduced by De Man, J. et al., J. Appl. Bact. 23:130-135, 1960)] (LMRS AGAR) is an enriched selective medium intended for the isolation and cultivation of *Lactobacillus* found in clinical specimens and dairy and food products. The basis of this medium consists of peptones yeast extract and glucose. This medium is supplemented with sorbitan monooleate complex (a source for fatty acids) and magnesium for additional growth requirements. Sodium acetate and ammonium citrate are added to inhibit normal flora, such as gram-negative bacteria, oral flora and fungi. With the addition of both of these inhibiting agents, the medium has been shown to selectively improve the growth of *Lactobacillus*. The pH is adjusted to 6.3-6.7 to favour the growth of *Lactobacillus*. This medium is prepared, dispensed, stored and packaged under oxygen-free conditions to prevent the formation of oxidized products prior to use.

Alternatively, for the culture enrichment of Lactobacilli of the vaginal flora a so-called CDM medium as described in Geshnizgani A. M., and Onderdonk A. B., (J Clin Microbiol. 1992 May; 30 (5): 1323-6) may be used. In this study, a chemically defined medium that simulates female genital tract secretions was developed for the growth of the vaginal microflora. Qualitative and quantitative studies of the growth of predominant components of the vaginal microflora indicated that all vaginal isolates tested were able to grow in this defined medium. The CDM medium was adapted by replacement of hemin (source of Fe-ions) by an equimolar amount of $FeSO_4 \cdot 7H_2O$ in order to decrease the turbidity of the medium.

EXAMPLES

Example 1 Carbohydrate Profile of L. crispatus Species

Carbohydrate degradation profiles were assessed for each Lactobacillus crispatus strain using the API CH50 carbohydrate fermentation tests (bioMérieux, Inc., Marcy l'Etoile, France) according to the manufacturer's protocol. In brief, the lactobacilli were cultivated on TSA plates (set to pH 5.0 with acetic acid and supplemented with 5% sheep serum and 0.25% lactic acid), at 37° C. under micro aerobic conditions (6% oxygen) for 48 hours. API 50 CHL medium (bio-Mérieux, Inc., Marcy l'Etoile, France) was inoculated with several identical colonies to obtain a suspension with turbidity equivalent to 2 MacFarland. The suspension was thoroughly mixed and added to each capsule of the fermentation strips. All capsules were covered with mineral oil (to ensure anaerobic conditions) and the strips were incubated at 37° C. for 48 hours. The strips were analyzed for colour changes after 48 hours. Each capsule has a different carbohydrate substrate and the API 50 CHL medium contains bromescal purple, a colour indicator that turns yellow at pH levels lower than 5, i.e. when fermentation has taken place.

In the Table 1 below, it has been recorded which substrates are metabolized by the individual strains that were detected. As can be seen, there were major differences between the carbohydrate degradation profile of the various strains. The strains with the below mentioned strain sequencing codes and strain Microbase codes were deposited under the Budapest Treaty with the Westerdijk Fungal Biodiversity Institute, having an address of Uppsalalaan 8, P.O. Box 85167, 3508 AD Utrecht, The Netherlands, on Jun. 9, 2017 (CBS 142869) and Jul. 4, 2017 (CBS 142868, CBS 142870, CBS 142871, CBS 142872, CBS 142873, and CBS 142874) and have received the respective CBS nos.

| CBS 142868 | Lactobacillus crispatus | RL04, 102__004, 87 |
| CBS 142869 | Lactobacillus crispatus | RL03, 102__003, 91 |
| CBS 142870 | Lactobacillus crispatus | RL06, 102__006, 98 |
| CBS 142871 | Lactobacillus crispatus | RL11, 102__011, 108 |
| CBS 142872 | Lactobacillus crispatus | RL12, 102__012, 109 |
| CBS 142873 | Lactobacillus crispatus | RL22, 102__022, 142 |
| CBS 142874 | Lactobacillus crispatus | RL26, 102__026, 144 |

Example 2 Glycogen Degradation Profiles

Methods

We specifically looked at glycogen degradation in 25 strains obtained from healthy women (n=12 HVM) or women with vaginal dysbiosis (n=13 DVM). In short, 1.1× carbohydrate deprived NYCIII medium was inoculated with 10% (v/v) bacterial broth (OD~0.5; 109 CFU/ml) and either water (negative control), 5% glucose (positive control) or 5% glycogen was added to the medium. Growth curves were followed in a BioScreen.

At least two independent experiments per strain were performed in triplicate.

Results (See FIG. 1)

Glycogen is the main carbohydrate source available to L. crispatus in the vaginal niche and we hypothesized that strain differences in glycogen degradation efficiency would associate with dominance in vivo. Of the 25 strains that were tested for glycogen degradation (n=12 HVM and n=13 DVM), five strains were less efficient at degrading glycogen (OD in stationary phase was 50% lower compared to growth on glucose) and one strain did not degrade glycogen at all (strain RL05.). Efficiency in glycogen degradation was however not associated with whether the strain was isolated from HVM or DVM.

TABLE 1

| BV status | 0 | 1 | 1 | 1 | 1 | 0 | 1 |
|---|---|---|---|---|---|---|---|
| Strain sequencing code | 102__026 | 102__030 | 102__002 | 102__007 | 102__025 | 102__003 | 102__019 |
| Strain code Microbase | 144 | 68 | 89 | 102 | 150 | 91 | 134 |
| CBS code | 142874 | | | | | 142869 | |
| Substrate | | | | | | | |
| 0 control | 0 | 0 | 0 | 0 | 0 | 0 | 0 |
| 1 GLYcerol | 0 | 0 | 0 | 0 | 0 | 0 | 0 |
| 2 ERYthritol | 0 | 0 | 0 | 0 | 0 | 0 | 0 |
| 3 D-ARAbinose | 0 | 0 | 0 | 0 | 0 | 0 | 0 |
| 4 L-ARAbinose | 0 | 0 | 0 | 0 | 0 | 0 | 0 |
| 5 D-RIBose | 0 | 0 | 0 | 0 | 0 | 0 | 0 |
| 6 D-XYLose | 0 | 0 | 0 | 0 | 0 | 0 | 0 |
| 7 L-XYLose | 0 | 0 | 0 | 0 | 0 | 0 | 0 |
| 8 D-ADOonitol | 0 | 0 | 0 | 0 | 0 | 0 | 0 |
| 9 Methyl-βD-Xylopyranoside | 0 | 0 | 0 | 0 | 0 | 0 | 0 |
| 10 D-GALactose | 0 | 1 | 0 | 1 | 1 | 0 | 0 |
| 11 D-GLUcose | 1 | 1 | 1 | 1 | 1 | 1 | 1 |
| 12 D-FRUCtose | 1 | 1 | 1 | 1 | 1 | 1 | 1 |
| 13 D-MaNnose | 0 | 0 | 0 | 0 | 0 | 0 | 0 |
| 14 L-SorBose | 0 | 0 | 0 | 0 | 0 | 0 | 0 |
| 15 L-RHAmnose | 0 | 0 | 0 | 0 | 0 | 0 | 0 |
| 16 DULcitol | 0 | 0 | 0 | 0 | 0 | 0 | 0 |
| 17 INOsitol | 0 | 0 | 0 | 0 | 0 | 0 | 0 |
| 18 D-MANnitol | 0 | 0 | 0 | 0 | 1 | 1 | 0 |
| 19 D-SORbitol | 0 | 0 | 0 | 0 | 0 | 0 | 0 |
| 20 Methyl-αD-Mannopyranoside | 0 | 0 | 0 | 0 | 0 | 0 | 0 |
| 21 Methyl-αD-Glucopyranoside | 0 | 0 | 0 | 0 | 0 | 0 | 0 |
| 22 N-AcetylGlucosamine | 1 | 1 | 1 | 2 | 1 | 1 | 1 |

TABLE 1-continued

| | | | | | | | |
|---|---|---|---|---|---|---|---|
| 23 AMYgdalin | 0 | 0 | 0 | 0 | 1 | 0 | 0 |
| 24 ARButin | 0 | 0 | 0 | 0 | 0 | 1 | 0 |
| 25 ESCulin ferric citrate | 1 | 1 | 1 | 1 | 1 | 1 | 1 |
| 26 SALicin | 0 | 0 | 0 | 0 | 1 | 1 | 0 |
| 27 D-CELIobiose | 0 | 0 | 1 | 0 | 1 | 0 | 0 |
| 28 D-MALTose | 1 | 1 | 1 | 0 | 1 | 1 | 1 |
| 29 D-LACTose (bovine origin) | 1 | 1 | 1 | 0 | 1 | 0 | 1 |
| 30 D-MELibiose | 0 | 0 | 2 | 0 | 0 | 0 | 0 |
| 31 D-SACcharose (sucrose) | 1 | 1 | 1 | 0 | 1 | 1 | 1 |
| 32 D-TREhalose | 0 | 0 | 1 | 0 | 1 | 0 | 2 |
| 33 INUlin | 0 | 0 | 0 | 0 | 0 | 0 | 0 |
| 34 D-MeLeZitose | 0 | 0 | 0 | 0 | 0 | 0 | 0 |
| 35 D-RAFfinose | 0 | 0 | 1 | 0 | 0 | 0 | 0 |
| 36 AmiDon (starch) | 2 | 1 | 1 | 0 | 1 | 1 | 0 |
| 37 GLYcoGen | 1 | 2 | 0 | 0 | 0 | 1 | 0 |
| 38 XyLiTol | 0 | 0 | 0 | 0 | 0 | 0 | 0 |
| 39 GENtibiose | 0 | 0 | 0 | 0 | 0 | 0 | 0 |
| 40 D-TURanose | 0 | 0 | 0 | 0 | 0 | 0 | 0 |
| 41 D-LYXose | 0 | 0 | 0 | 0 | 0 | 0 | 0 |
| 42 D-TAGatose | 0 | 0 | 0 | 0 | 0 | 0 | 0 |
| 43 D-FUCose | 0 | 0 | 0 | 0 | 0 | 0 | 0 |
| 44 L-FUCose | 0 | 0 | 0 | 0 | 0 | 0 | 0 |
| 45 D-ARAbitol | 0 | 0 | 0 | 0 | 0 | 0 | 0 |
| 46 L-ARAbitol | 0 | 0 | 0 | 0 | 0 | 0 | 0 |
| 47 potassium GlucoNaTe | 0 | 0 | 0 | 0 | 0 | 0 | 0 |
| 48 potassium 2-KetoGluconate | 0 | 0 | 0 | 0 | 0 | 0 | 0 |
| 49 potassium 5-KetoGluconate | 0 | 0 | 0 | 0 | 0 | 0 | 0 |
| BV status | 0 | 0 | 0 | 1 | 0 | 1 | 1 |
| Strain sequencing code | 102_016 | 102_006 | 102_009 | 102_028 | 102_011 | 102_015 | 102_020 |
| Strain code Microbase | 123 | 98 | 103 | 54 | 108 | 116 | 130 |
| CBS code | | 142870 | | | 142871 | | |
| Substrate | | | | | | | |
| 0 control | 0 | 0 | 0 | 0 | 0 | 0 | 0 |
| 1 GLYcerol | 0 | 0 | 0 | 0 | 0 | 0 | 0 |
| 2 ERYthritol | 0 | 0 | 0 | 0 | 0 | 0 | 0 |
| 3 D-ARAbinose | 0 | 0 | 0 | 0 | 0 | 0 | 0 |
| 4 L-ARAbinose | 0 | 0 | 0 | 0 | 0 | 0 | 0 |
| 5 D-RIBose | 0 | 0 | 0 | 0 | 0 | 0 | 0 |
| 6 D-XYLose | 0 | 0 | 0 | 0 | 0 | 0 | 0 |
| 7 L-XYLose | 0 | 0 | 0 | 0 | 0 | 0 | 0 |
| 8 D-ADOonitol | 0 | 0 | 0 | 0 | 0 | 0 | 0 |
| 9 Methyl-βD-Xylopyranoside | 0 | 0 | 0 | 0 | 0 | 0 | 0 |
| 10 D-GALactose | 0 | 1 | 1 | 0 | 1 | 1 | 1 |
| 11 D-GLUcose | 1 | 1 | 1 | 1 | 1 | 1 | 1 |
| 12 D-FRUCtose | 1 | 0 | 1 | 1 | 1 | 1 | 1 |
| 13 D-MaNnose | 0 | 0 | 0 | 0 | 1 | 0 | 1 |
| 14 L-SorBose | 0 | 0 | 0 | 0 | 0 | 0 | 0 |
| 15 L-RHAmnose | 0 | 0 | 0 | 0 | 0 | 0 | 0 |
| 16 DULcitol | 0 | 0 | 0 | 0 | 0 | 0 | 0 |
| 17 INOsitol | 0 | 0 | 0 | 0 | 0 | 0 | 0 |
| 18 D-MANnitol | 0 | 0 | 0 | 1 | 1 | 1 | 2 |
| 19 D-SORbitol | 0 | 0 | 0 | 0 | 0 | 0 | 0 |
| 20 Methyl-αD-Mannopyranoside | 0 | 0 | 0 | 0 | 0 | 0 | 0 |
| 21 Methyl-αD-Glucopyranoside | 0 | 0 | 0 | 0 | 0 | 0 | 0 |
| 22 N-AcetylGlucosamine | 1 | 0 | 1 | 1 | 1 | 1 | 1 |
| 23 AMYgdalin | 0 | 0 | 0 | 0 | 0 | 2 | 0 |
| 24 ARButin | 0 | 0 | 0 | 1 | 1 | 0 | 0 |
| 25 ESCulin ferric citrate | 1 | 1 | 1 | 1 | 1 | 1 | 1 |
| 26 SALicin | 0 | 0 | 0 | 1 | 1 | 1 | 1 |
| 27 D-CELIobiose | 0 | 0 | 1 | 1 | 1 | 1 | 1 |
| 28 D-MALTose | 1 | 1 | 1 | 1 | 1 | 1 | 1 |
| 29 D-LACTose (bovine origin) | 0 | 1 | 0 | 1 | 1 | 1 | 1 |
| 30 D-MELibiose | 0 | 0 | 2 | 0 | 0 | 0 | 0 |
| 31 D-SACcharose (sucrose) | 1 | 0 | 1 | 1 | 0 | 1 | 1 |
| 32 D-TREhalose | 0 | 0 | 1 | 1 | 0 | 1 | 1 |
| 33 INUlin | 0 | 0 | 0 | 0 | 0 | 0 | 0 |
| 34 D-MeLeZitose | 0 | 0 | 0 | 0 | 0 | 0 | 0 |
| 35 D-RAFfinose | 0 | 0 | 2 | 0 | 0 | 0 | 0 |
| 36 AmiDon (starch) | 1 | 1 | 1 | 1 | 1 | 1 | 1 |
| 37 GLYcoGen | 0 | 0 | 0 | 1 | 1 | 2 | 1 |
| 38 XyLiTol | 0 | 0 | 0 | 0 | 0 | 0 | 0 |
| 39 GENtibiose | 0 | 0 | 0 | 0 | 0 | 0 | 2 |
| 40 D-TURanose | 0 | 0 | 0 | 0 | 0 | 0 | 0 |
| 41 D-LYXose | 0 | 0 | 0 | 0 | 0 | 0 | 0 |
| 42 D-TAGatose | 0 | 0 | 0 | 0 | 0 | 0 | 0 |
| 43 D-FUCose | 0 | 0 | 0 | 0 | 0 | 0 | 0 |
| 44 L-FUCose | 0 | 0 | 0 | 0 | 0 | 0 | 0 |

TABLE 1-continued

| Substrate | | | | | | | |
|---|---|---|---|---|---|---|---|
| 45 D-ARAbitol | 0 | 0 | 0 | 0 | 0 | 0 | 0 |
| 46 L-ARAbitol | 0 | 0 | 0 | 0 | 0 | 0 | 0 |
| 47 potassium GlucoNaTe | 0 | 0 | 0 | 0 | 0 | 0 | 0 |
| 48 potassium 2-KetoGluconate | 0 | 0 | 0 | 0 | 0 | 0 | 0 |
| 49 potassium 5-KetoGluconate | 0 | 0 | 0 | 0 | 0 | 0 | 0 |
| BV status | 0 | 0 | 1 | 1 | 1 | 0 | 0 |
| Strain sequencing code | 102_022 | 102_010 | 102_023 | 102_024 | 102_033 | 102_012 | 102_004 |
| Strain code Microbase | 142 | 106 | 138 | 148 | 75 | 109 | 87 |
| CBS code | 142873 | | | | | 142872 | 142868 |
| Substrate | | | | | | | |
| 0 control | 0 | 0 | 0 | 0 | 0 | 0 | 0 |
| 1 GLYcerol | 0 | 0 | 0 | 0 | 0 | 0 | 0 |
| 2 ERYthritol | 0 | 0 | 0 | 0 | 0 | 0 | 0 |
| 3 D-ARAbinose | 0 | 0 | 0 | 0 | 0 | 0 | 0 |
| 4 L-ARAbinose | 0 | 0 | 0 | 0 | 0 | 0 | 0 |
| 5 D-RIBose | 0 | 0 | 0 | 0 | 0 | 0 | 2 |
| 6 D-XYLose | 0 | 0 | 0 | 0 | 0 | 0 | 0 |
| 7 L-XYLose | 0 | 0 | 0 | 0 | 0 | 0 | 0 |
| 8 D-ADOonitol | 0 | 0 | 0 | 0 | 0 | 0 | 0 |
| 9 Methyl-βD-Xylopyranoside | 0 | 0 | 0 | 0 | 0 | 0 | 0 |
| 10 D-GALactose | 1 | 1 | 1 | 1 | 2 | 1 | 1 |
| 11 D-GLUcose | 1 | 1 | 1 | 1 | 1 | 1 | 1 |
| 12 D-FRUCtose | 1 | 1 | 1 | 1 | 1 | 1 | 1 |
| 13 D-MaNnose | 1 | 0 | 0 | 0 | 0 | 0 | 0 |
| 14 L-SorBose | 0 | 0 | 0 | 0 | 0 | 0 | 0 |
| 15 L-RHAmnose | 0 | 0 | 0 | 0 | 0 | 0 | 0 |
| 16 DULcitol | 0 | 0 | 1 | 0 | 0 | 0 | 0 |
| 17 INOsitol | 0 | 0 | 0 | 0 | 0 | 0 | 0 |
| 18 D-MANnitol | 1 | 0 | 1 | 0 | 0 | 0 | 1 |
| 19 D-SORbitol | 0 | 0 | 0 | 0 | 0 | 0 | 0 |
| 20 Methyl-αD-Mannopyranoside | 0 | 0 | 0 | 0 | 0 | 0 | 0 |
| 21 Methyl-αD-Glucopyranoside | 0 | 0 | 2 | 0 | 0 | 0 | 0 |
| 22 N-AetylGlucosamine | 1 | 1 | 1 | 1 | 1 | 1 | 1 |
| 23 AMYgdalin | 1 | 0 | 1 | 0 | 0 | 0 | 1 |
| 24 ARButin | 1 | 0 | 1 | 0 | 0 | 0 | 0 |
| 25 ESCulin ferric citrate | 1 | 1 | 1 | 1 | 1 | 1 | 1 |
| 26 SALicin | 1 | 0 | 1 | 1 | 0 | 0 | 1 |
| 27 D-CELlobiose | 1 | 0 | 1 | 1 | 0 | 0 | 1 |
| 28 D-MALTose | 1 | 1 | 1 | 1 | 1 | 1 | 1 |
| 29 D-LACTose (bovine origin) | 1 | 0 | 1 | 1 | 0 | 1 | 0 |
| 30 D-MELibiose | 0 | 0 | 0 | 0 | 0 | 0 | 0 |
| 31 D-SACcharose (sucrose) | 1 | 1 | 1 | 1 | 1 | 1 | 1 |
| 32 D-TREhalose | 1 | 0 | 1 | 0 | 0 | 0 | 0 |
| 33 INUlin | 0 | 0 | 0 | 0 | 0 | 0 | 0 |
| 34 D-MeLeZitose | 0 | 0 | 0 | 0 | 0 | 0 | 0 |
| 35 D-RAFfinose | 0 | 0 | 0 | 0 | 0 | 0 | 0 |
| 36 AmiDon (starch) | 1 | 1 | 1 | 1 | 1 | 1 | 1 |
| 37 GLYcoGen | 0 | 0 | 0 | 1 | 1 | 0 | 1 |
| 38 XyLiTol | 0 | 0 | 0 | 0 | 0 | 0 | 0 |
| 39 GENtibiose | 0 | 0 | 0 | 0 | 0 | 0 | 0 |
| 40 D-TURanose | 0 | 0 | 0 | 0 | 0 | 0 | 0 |
| 41 D-LYXose | 0 | 0 | 0 | 0 | 0 | 0 | 0 |
| 42 D-TAGatose | 0 | 0 | 0 | 0 | 0 | 0 | 0 |
| 43 D-FUCose | 0 | 0 | 0 | 0 | 0 | 0 | 0 |
| 44 L-FUCose | 0 | 0 | 0 | 0 | 0 | 0 | 0 |
| 45 D-ARAbitol | 0 | 0 | 0 | 0 | 0 | 0 | 0 |
| 46 L-ARAbitol | 0 | 0 | 0 | 0 | 0 | 0 | 0 |
| 47 potassium GlucoNaTe | 0 | 0 | 0 | 0 | 0 | 0 | 0 |
| 48 potassium 2-KetoGluconate | 0 | 0 | 0 | 0 | 0 | 0 | 0 |
| 49 potassium 5-KetoGluconate | 0 | 0 | 0 | 0 | 0 | 0 | 0 |

0 = no degradation
1 = degradation
2 = little degradation

The invention claimed is:

1. A method for the treatment or prevention of bacterial vaginosis, comprising topical administration of a mixture of strains of *Lactobacillus crispatus*, which mixture comprises strains that have a different carbohydrate degradation profile, comprising at least one strain of *L. crispatus* that is able to degrade glycogen, and at least one strain of *L. crispatus* that is able to degrade lactose.

2. A method of treatment or prevention of bacterial vaginosis to decrease recurrence of bacterial vaginosis after treatment with antibiotics, said method comprises a first treatment with an antibiotic compound and a second treatment with a mixture of strains of *Lactobacillus crispatus*, which mixture comprises strains that have a different carbohydrate degradation profile, comprising at least one strain of *L. crispatus* that is able to degrade glycogen, and at least one strain of *L. crispatus* that is able to degrade lactose.

3. The method according to claim 1, wherein said strains were isolated from a subject without bacterial vaginosis.

4. The method according to claim 1, wherein said mixture of strains in total comprises 4 or more strains of *L. crispatus* that differ from each other on basis of their carbohydrate degradation profile.

5. The method according to claim 4, wherein said mixture of strains comprises at least 2 strains that are able to degrade glycogen and at least 2 strains that are able to degrade lactose.

6. The method according to claim 1, wherein said mixture of strains comprises at least one glycogen degrading strain chosen from CBS 142868, CBS 142871 and CBS 142874, as deposited with the Westerdijk Fungal Biodiversity Institute on Jul. 4, 2017 and CBS 142869 as deposited with the Westerdijk Fungal Biodiversity Institute on Jun. 9, 2017, and at least one lactose degrading strain chosen from CBS 142870, CBS 142871, CBS 142872, CBS 142873 and CBS 142874 as deposited with the Westerdijk Fungal Biodiversity Institute on Jul. 4, 2017.

7. A probiotic composition comprising a mixture of strains of *Lactobacillus crispatus* and lactose, which mixture comprises strains that have a different carbohydrate degradation profile, comprising at least one strain of *L. crispatus* that is able to degrade glycogen, and at least one strain of *L. crispatus* that is able to degrade lactose.

8. The probiotic composition according to claim 7, further comprising glycogen.

9. The method according to claim 6, wherein said mixture of strains comprises at least six strains.

10. The probiotic composition of claim 8 further comprising a carbohydrate mixture comprising two or more carbohydrates selected from the group of glycogen, galactose, glucose, lactulose, mannose, n-acetylglucosamine, cellobiose, maltose, mannose, mannitol, raffinose, trehalose, saccharose, starch, amygdalin, arbutin, salicin and esculin.

11. A method for the treatment or prevention of bacterial vaginosis comprising topical administration of the probiotic composition according to claim 7.

12. A method of treatment or prevention of bacterial vaginosis, said method comprising a first treatment with an antibiotic compound and a second treatment with a probiotic composition according to claim 7.

13. The method of treatment or prevention of bacterial vaginosis according to claim 1, wherein said method decreases recurrence of bacterial vaginosis after treatment with antibiotics.

14. The method of treatment or prevention of bacterial vaginosis according to claim 11, wherein said method decreases recurrence of bacterial vaginosis after treatment with antibiotics.

* * * * *